US009721464B2

(12) United States Patent
Magno et al.

(10) Patent No.: US 9,721,464 B2
(45) Date of Patent: Aug. 1, 2017

(54) CLEANING, DISINFECTING, CARE AND/OR STERILIZATION DEVICE FOR MEDICAL OR DENTAL INSTRUMENTS

(71) Applicant: W&H Sterilization S.r.l., Brusaporto (BG) (IT)

(72) Inventors: Marino Magno, Almenno San Salvatore (IT); Alejandro Ramirez Ramos, Albano Sant' Alessandro (IT); Fabio Ghezzi, Cusano Milanino (IT); Klaus Maier, Salzburg (AT)

(73) Assignee: W&H Sterilization S.r.l., Brusaporto (BG) (IT)

( * ) Notice: Subject to any disclaimer, the term of this patent is extended or adjusted under 35 U.S.C. 154(b) by 0 days.

(21) Appl. No.: 15/260,193

(22) Filed: Sep. 8, 2016

(65) Prior Publication Data
US 2017/0069199 A1    Mar. 9, 2017

(30) Foreign Application Priority Data

Sep. 8, 2015   (EP) .................................... 15184148

(51) Int. Cl.
*G08C 17/02*   (2006.01)
*A61L 2/16*    (2006.01)
(Continued)

(52) U.S. Cl.
CPC .......... *G08C 17/02* (2013.01); *A47L 15/0063* (2013.01); *A61B 90/70* (2016.02);
(Continued)

(58) Field of Classification Search
CPC ......... G08C 17/02; A61B 90/70; A61B 19/34; A61C 19/002; A61L 2/07; A61L 2/16;
(Continued)

(56) References Cited

U.S. PATENT DOCUMENTS

| 7,357,296 B2 | 4/2008 | Stemmle |
| 9,122,788 B2 | 9/2015 | Elston, III et al. |
| 9,522,044 B2 * | 12/2016 | Wimmer .............. A61C 19/002 |

FOREIGN PATENT DOCUMENTS

| EP | 2422744 | 2/2012 |
| WO | WO2015/039874 | 3/2015 |
| WO | WO2015/049003 | 4/2015 |

OTHER PUBLICATIONS

European Search Report for EP15184148 (Feb. 12, 2016).

* cited by examiner

*Primary Examiner* — Ali Neyzari
(74) *Attorney, Agent, or Firm* — Klarquist Sparkman, LLP

(57) ABSTRACT

A cleaning, disinfecting, care and/or sterilization device for at least one medical or dental instrument comprising a housing, a treatment chamber for receiving the at least one medical or dental instrument, a media supply for feeding and/or discharging media into the treatment chamber and a control unit operable to control and/or regulate a cleaning, disinfecting, care and/or sterilization process, wherein the control unit comprises a wireless communication device to communicate with remote accessories of the cleaning, disinfecting, care and/or sterilization device and wherein the wireless communication device is capable of creating a wireless local area network allowing the remote accessories to communicate with the control unit of the cleaning, disinfecting, care and/or sterilization device.

15 Claims, 2 Drawing Sheets

(51) Int. Cl.
*A61L 2/07* (2006.01)
*A61L 2/24* (2006.01)
*B08B 13/00* (2006.01)
*B08B 3/08* (2006.01)
*A61C 19/00* (2006.01)
*A61B 90/70* (2016.01)
*A47L 15/00* (2006.01)
*A61L 2/26* (2006.01)
*G06F 19/00* (2011.01)
*H04L 12/28* (2006.01)
*H04W 84/12* (2009.01)
*B08B 3/00* (2006.01)

(52) U.S. Cl.
CPC .............. *A61C 19/002* (2013.01); *A61L 2/07* (2013.01); *A61L 2/16* (2013.01); *A61L 2/24* (2013.01); *A61L 2/26* (2013.01); *B08B 3/08* (2013.01); *B08B 13/00* (2013.01); *G06F 19/327* (2013.01); *H04L 12/28* (2013.01); *A61L 2202/14* (2013.01); *A61L 2202/24* (2013.01); *B08B 3/00* (2013.01); *H04W 84/12* (2013.01)

(58) Field of Classification Search
CPC .......... A61L 2/24; A61L 2202/14; A61L 2/26; B08B 3/08; B08B 13/00; B08B 3/00; H04W 84/12; A47L 15/0063; G06F 19/327; H04L 12/28
USPC .......................................... 340/12.5; 422/292
See application file for complete search history.

CLEANING, DISINFECTING, CARE AND/OR STERILIZATION DEVICE FOR MEDICAL OR DENTAL INSTRUMENTS

CROSS REFERENCE TO RELATED APPLICATION

The present application claims priority from pending European Patent Application No. 15184148.3, filed Sep. 8, 2015, which is incorporated herein by reference.

BACKGROUND

Field

The present invention relates to a cleaning, disinfecting, care and/or sterilization device for medical or dental instruments. In particular, the invention relates to an improved cleaning, disinfecting, care and/or sterilization device ensuring secure communication between such a device and accessories remotely connected to the device.

Description of Prior Art

The cleaning, disinfecting, care and/or sterilization device, also referred to as reprocessing device in the following, as described herein is understood to refer to devices which execute or enable a sanitizing or cleaning treatment for medical or dental instruments, in particular with water, steam, compressed air and/or a cleaning agent, a disinfection treatment, such as thermal disinfection, a care treatment by introducing a lubricant, such as oil, and/or a sterilization treatment, in particular by steam.

The treated medical instruments preferably serve to process hard or soft tissue or for inserting implants. They comprise hollow bodies in which drive mechanism and/or supply lines for the drive mechanism are placed. Further, they are preferably designed as medical handpieces or contra-angle handpieces. After the operation of the medical instruments they have to be cleaned, disinfected and/or sterilized. Also maintenance of the medical instruments is required in regular intervals.

The cleaning, disinfecting, care and/or sterilization devices usually comprise housings, treatment chambers and several machine components, such as pumps, steam generators, condensers, heating elements, filters, electric motors, sealings, sensors, compressors, and operating elements, such as switches or displays, control units and/or supply elements, such as energy or media supply units. Accessories, such as racks and/or trays for holding the medical instruments, a printer for archiving treatment reports, a pouch sealing device, a water supply and/or distiller, adapters for the instruments, test kits to evaluate the reprocessing process, evaluation units, dental units and/or remote displays, are often connected to the reprocessing device and communicate with the device by a wire connection to transfer data and signals from the accessory to the reprocessing device.

Such a cleaning or maintenance apparatus for medical, in particular dental instruments is described in particular in the patent application EP 2 422 744 A1, which is incorporated herein by reference. The cleaning or maintenance apparatus comprises at least one cleaning cartridge for holding the medical instruments and in particular connecting the medical instruments to a media supply of the apparatus.

Further, the patent application WO 2015/049003 A1 describes a device for washing, disinfecting and/or sterilizing medical, dental, laboratory and/or pharmaceutical goods, which comprises an accessory for the device, in particular a touch screen display, which can be remotely connected to the device, e.g., via a wire or a wireless connection. The remote connection is performed over a wireless network to which both the display and the device for washing, disinfecting and/or sterilizing medical goods are connected.

The advantage of this device for washing, disinfecting and/or sterilizing medical goods is that the device can communicate with an accessory, in particular with a mobile phone, which is remotely connected to the device. Using the mobile phone process parameters or process states can be remotely displayed to the user. Further, the user is enabled to remotely control the washing, disinfecting, care or sterilization device without the need to stay next to the reprocessing device for operating the device.

SUMMARY

It would be advantageous to provide a cleaning, disinfecting, care and/or sterilization device for medical instruments which allows to communicate with accessories of the reprocessing device which are remotely connected to the device by a wireless connection, as mentioned above, but in a more secure manner than using an existing public wireless network to which both the reprocessing device and the accessory, in particular the mobile phone, are connected, as proposed in the prior art.

Hence, it is an object to overcome the drawbacks set forth above by creating a cleaning, disinfecting, care and/or sterilization device for medical or dental instruments which will make it possible in particular to safely and reliably transfer information between the reprocessing device and the accessories of the device.

According to an embodiment of a cleaning, disinfecting, care and/or sterilization device for medical or dental instruments the device comprises a housing, a treatment chamber for receiving the at least one medical or dental instrument, a media supply for feeding media into and/or discharging media or out of the treatment chamber and a control unit operable to control and/or regulate a cleaning, disinfecting, care and/or sterilization process, wherein the control unit comprises a wireless communication device to communicate with at least one remote accessory of the cleaning, disinfecting, care and/or sterilization device and wherein the wireless communication device is capable of creating a wireless local area network (WLAN) allowing the remote accessory to communicate with the control unit of the cleaning, disinfecting, care and/or sterilization device.

By providing a cleaning, disinfecting, care and/or sterilization device with a wireless communication device, which for example according to a first embodiment are non detachably connected to the control unit of the device and are capable of creating a wireless local area network, it is possible that the cleaning, disinfecting, care and/or sterilization device, in particular the control unit of the reprocessing device, can communicate with the at least one remote accessory, such as interfaces to transmit maintenance requirements and service instructions from the device to a remote evaluation unit and/or remote display, in a safe manner.

The medical device thus does not have to use an existing public wireless network to which besides the reprocessing device and the accessories additional devices and users are connected. So a safe and reliable transfer of information between the reprocessing device and the accessories of the device can be achieved.

According to a second embodiment of the cleaning, disinfecting, care and/or sterilization device, the wireless communication device is detachably connected to the control unit of the reprocessing device. In particular, a USB connection is used to connect the wireless communication device to the control unit of the device. In particular, the wireless communication device is preferably formed as an adapter, such as a USB stick. To protect it from mechanical and chemical damage, the wireless communication device including a wireless access point to create the wireless local area network is preferably encapsulated in a housing. According to this embodiment the stick is detachably connected to a USB port of the control unit which is fixed to the housing of the reprocessing device.

According to a third embodiment of the cleaning, disinfecting, care and/or sterilization device, the control unit comprises an internet bridge to provide internet access for the cleaning, disinfecting, care and/or sterilization device and/or for the at least one accessory that is within the range of a wireless local area network. Preferably, the internet bridge is built by or comprises a cellular modem, which is non-detachably or detachably connected to the control unit of the cleaning, disinfecting, care and/or sterilization device.

Through the connection of the cleaning, disinfecting, care and/or sterilization device and the accessory for the device with the internet it is possible for example to transmit maintenance requirements and service instructions from the reprocessing device, in particular from the control unit, or from the accessory to a remote evaluation unit, in particular to a central server.

According to a fourth embodiment of the cleaning, disinfecting, care and/or sterilization device, the control unit of the device is designed to activate the wireless communication device to create the wireless local area network. The activation of the wireless communication device preferably occurs through the operation of the reprocessing device. It is also possible that the wireless communication device will be activated selectively. For example, the control unit is designed to activate the wireless communication device and/or automatically communicate with at least one connected remote accessory depending on a process parameter or process state of the cleaning, disinfecting, care and/or sterilization device. So the wireless local area network will not be generated permanently. This enables protecting the user from electromagnetic fields, which are generated by the wireless communications means, while no communication between the reprocessing device and the accessories takes place.

According to all the preceding embodiments the wireless communication device is capable of creating the wireless local area network according the Wi-Fi standard. The Wi-Fi standard mainly uses the 2.4 gigahertz UHF and 5 gigahertz SHF ISM radio bands for networking. Using the Wi-Fi networking technology ensures compatibility of the accessories with the reprocessing device, even if an accessory is not provided by the manufacturer of the reprocessing device for example. Thus, the Wi-Fi standard allows multiple accessories of the reprocessing device to network, in particular simultaneously. The number of accessories is not limited. For example, more than ten devices can network with the reprocessing device. Furthermore, the Wi-Fi standard includes a security pass code matching process. This makes Wi-Fi connections much more secure than other networking standards. Finally, Wi-Fi makes it able to work at longer distances than related networking technologies.

According to a first embodiment of an apparatus for cleaning, disinfecting, caring and/or sterilizing at least one medical or dental instrument, the apparatus comprises a cleaning, disinfecting, care and/or sterilization device capable of creating a wireless local area network according to one of the previous embodiments and at least one accessory of the reprocessing device, wherein the at least one accessory comprises a wireless network interface to provide access to the wireless local area network in order to communicate with the control unit of the cleaning, disinfecting, care and/or sterilization device.

The wireless network interface is either non-detachably connected to the accessory for the cleaning, disinfecting, care and/or sterilization device, in particular to an electric component of the accessory, or detachably connected to the accessory. In the latter case the wireless network interface device preferably comprises a USB interface and an internal antenna to communicate with the wireless area network. Another connectivity option is to integrate the wireless network interface, in particular in form of an interface card, into the accessory.

According to a second embodiment of the apparatus, the accessory of the apparatus, in particular the wireless network interface, is designed to communicate with control units of multiple cleaning, disinfecting, care and/or sterilization devices simultaneously. So it is possible, when using a smart phone for example, to control multiple reprocessing devices simultaneously, in particular in real time. This makes it possible to work more easily, more efficiently and in a more flexible way.

According to all the preceding embodiments of the cleaning, disinfecting, care and/or sterilization device and of the apparatus for cleaning, disinfecting, caring and/or sterilizing at least one medical or dental instrument, the accessory is preferably one of: a rack or tray for holding the medical instrument, a printer, a pouch sealing device, a water supply and/or distiller, an adapter for the instrument, a test kit to evaluate a reprocessing process, an evaluation unit, a dental unit, a mobile phone or a remote display.

The present cleaning, disinfecting, care and/or sterilization device for medical or dental instruments is characterized by the following advantages.

As mentioned before, by providing a cleaning, disinfecting, care and/or sterilization device with a wireless communication device which is capable of creating a wireless local area network, it is possible to safely and reliably transfer information between the reprocessing device and the accessories of the device. Existing public wireless networks used by additional devices are not needed.

Another advantage is that the cleaning, disinfecting, care and/or sterilization device and the accessory are connectable with the internet. Thus, according to one of the especially preferred embodiments of the invention, it is possible to transmit maintenance requirements and service instructions from the reprocessing device and/or from the accessory to a remote server for example.

Furthermore, through the improved cleaning, disinfecting, care and/or sterilization device it is possible to activate the wireless communication device to create the wireless local area network selectively. The wireless local area network will not be generated permanently. This enables protecting the user from electromagnetic fields which are generated by the wireless communications means while no communication between the reprocessing device and the accessories takes place.

A further advantage results from the use of the Wi-Fi networking technology. This ensures, as mentioned before, compatibility of the accessories with the reprocessing device, even if an accessory is not provided by the manufacturer of the reprocessing device for example.

Finally, by providing an apparatus with at least one reprocessing device for medical instruments which is capable of creating a wireless local area network and an accessory with a wireless network interface, which is designed to communicate with multiple control units of multiple reprocessing devices, it is possible to control multiple reprocessing devices simultaneously, in particular in real time.

These and other embodiments will be described below with reference to the following drawings.

DETAILED DESCRIPTION

Figure 1:
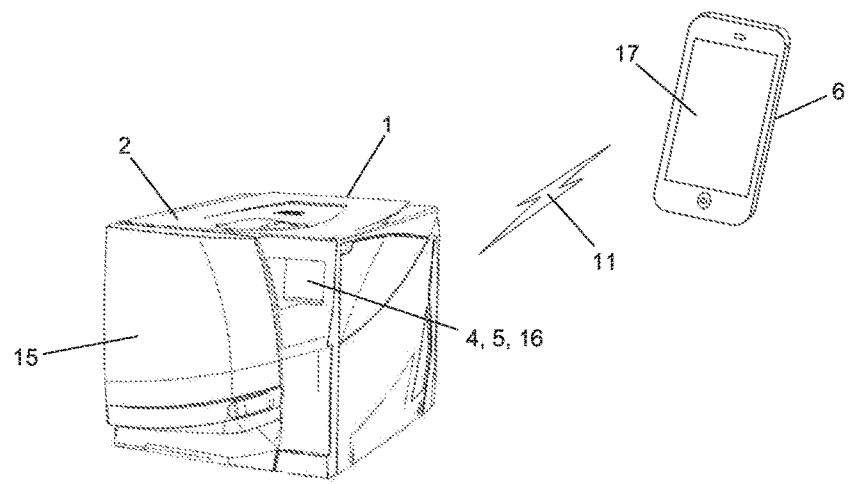
FIG. 1 shows a first embodiment of the reprocessing device, in particular a sterilization device, which is capable of creating a wireless local area network, and an accessory, in particular a mobile or smart phone, for monitoring and/or operating the sterilization device.

FIG. 1 schematically shows a reprocessing device, in particular a sterilization device 1, which is capable of creating a wireless local area network 11, and an accessory, in particular a mobile phone or smart phone 6, for monitoring and/or operating the device 1. The sterilization device 1 comprises a housing 2 in which a sterilization chamber (not shown) is arranged. The chamber is defined by a casing and an air-tight door 15. In order to withstand pressure differences between the inside of the chamber and the outside the chamber and the door 15 are preferably made of stainless steel. The chamber comprises several inlet and outlet openings, which are connected to a media supply for feeding and/or discharging media, such as steam, air and so on. The media supply may comprise in particular, among other things, a certain number of channels to convey the above mentioned media, containers for the sterilization agents or waste water, connections to fluid sources, in particular to an air or water sources, and components, such as heating elements, a condenser, fluid or evacuation pumps, a filter and so on. Furthermore, the media supply comprises actuators, for example valves or sensors, such as temperature, pressure, conductivity, flow or concentration sensors.

In addition to the media supply, the device comprises a control unit 4, which is arranged in the sterilization device 1 to control and/or regulate a sterilization process. The control unit 4 preferably comprises a processor, a memory unit, a display 16, in particular a touch screen, a communication interface, and a connection to a power source, to the above mentioned technical components, to the several sensors of the media supply and to additional sensors, which are arranged in or are connect to the sterilization chamber and/or to the technical components to monitor the operation of the sterilization device 1. Further, the control unit 4 comprises a wireless communication device 5, which is capable of creating a wireless local area network 11, in particular according to the Wi-Fi standard, to communicate with the smart phone 6. According to the first embodiment, the wireless communication device 5 is non-detachably connected to the control unit 4 of the sterilization device 1, which is positioned in the housing 2 of the sterilization device 1. The wireless communication device 5 itself comprises a wireless access point to create the wireless local area network 11.

The smart phone 6 comprises a wireless network interface to provide access to the wireless local area network 11 in order to communicate with the control unit 4 of the sterilization device 1. In this embodiment the wireless network interface is non-detachably connected to the smart phone 6, in particular integrated into the smart phone 6 in form of an interface card.

According to this first embodiment, one or more process parameters, such as temperature, pressure, quantity of material, moisture, electrical conductivity, operation time, electric energy, is transferable from the sterilization device 1, in particular from the control unit 4, to the remote smart phone 6. Further, process states of the sterilization process, such as "Sterilization starts," "Sterilization runs," or "Sterilization finished" can be transmitted from the control unit 4 of the sterilization device 1 to the smart phone 6. Both the process parameters and the process states can be displayed on the touch screen 17 of the smart phone 6. So a user is enabled to remotely monitor the sterilization device 1 without the need to stay next to the reprocessing device 1. Furthermore, according to this embodiment, the smart phone 6, in particular the wireless network interface, and the control unit 4 of the sterilization device 1 are designed in such a way that a user is allowed to remotely operate the sterilization device 1, for example to select and/or start a sterilization process. In particular, the smart phone 6 and the wireless network interface are designed to communicate with the control units 4 of multiple cleaning, disinfecting, care and/or sterilization devices 1 simultaneously. So it is possible to monitor and control multiple sterilization devices 1 in particular in real time.

Figure 2:
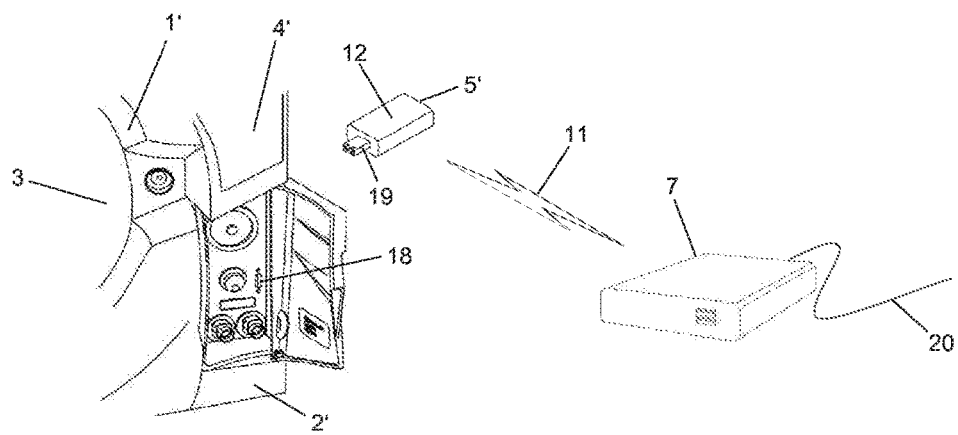
FIG. 2 shows a second embodiment of the reprocessing device, in particular an enlarged detail of a sterilization device as shown in FIG. 1, of the wireless communication device, which is detachably connected to the sterilization device, and a remote evaluation unit.

FIG. 2 shows a second embodiment of the cleaning, disinfecting, care and/or sterilization device 1', in particular a detailed view of the sterilization device as shown in FIG. 1. According to this second embodiment the wireless communication device 5' of the control unit 4' is detachably connected to the sterilization device 1'. A USB connection 18, 19 is used to connect it to the control unit 4' of the device 1' by a wired connection. In particular, the wireless communication device 5' is formed as an adapter, such as a USB stick, and is encapsulated in a separate housing 12 to protect it from mechanical and chemical damage. The USB stick 12 is connectable to a USB port 18 of the control unit 5' which is arranged at the housing 2' of the sterilization device 1'. The adapter 12 includes a wireless access point to create the wireless local area network 11 for monitoring and operating the sterilization device 1'.

According to this embodiment the accessory of the sterilization device 1' is a remote evaluation unit 7. The remote evaluation unit 7 monitors multiple process parameters of the sterilization device 1' for a plurality of operation cycles. Therefore the evaluation unit 7 comprises a wireless network interface to provide access to the wireless local area network 11 created by the control unit 4' of the sterilization device 1'. A maintenance requirement is detected by the evaluation unit 7 for example, when the parameters follow a trend to a failure of the reprocessing device 1'. This enables avoiding a failure or a breakdown of the sterilization device 1'. So the wireless communication device 5' of the control unit 4' serves to transmit the monitored process parameters from the sterilization device 1', in particular from the control unit 4', to the remote evaluation unit 7. Therefore the control unit 4' is designed to activate the wireless communication device 5', preferably after each sterilization process to transmit the recorded process parameters. Alternatively, the control unit 4' is designed to automatically communicate with the evaluation unit 7 depending on the monitored process parameters.

Additionally, according to this embodiment the remote evaluation unit 7 is designed to transmit the monitored maintenance requirement to a server of a service center for the sterilization device 1', preferably by a wired connection, such as an Internet bridge 20. So the service center can send a technician to repair or change the sterilization device 1' with the detected technical defect. The monitored maintenance requirement can be also transmitted from the evaluation unit 7 to the sterilization device 1' by the wireless connection 11 to display the user the technical defect. So the wireless local area network 11 allows bidirectional communication between the sterilization device 1' and the remote evaluation unit 7.

Figure 3:
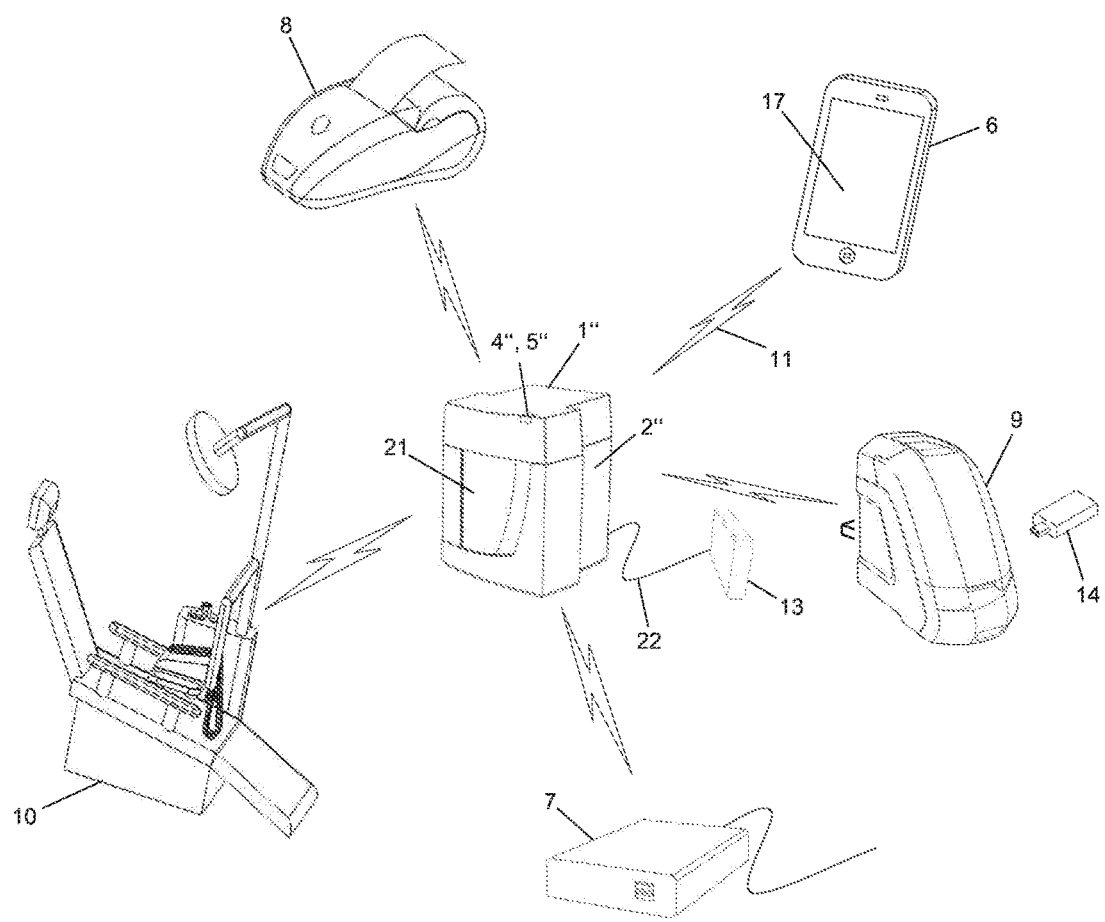
FIG. 3 shows a third embodiment of the cleaning, disinfecting, care and/or sterilization device, in particular a reprocessing device, which cleans, cares and sterilizes medical, in particular dental instruments, wherein a variety of accessories communicate with the reprocessing device.

FIG. 3 shows a reprocessing device 1", in particular a cleaning, disinfection, care and sterilization device 1", wherein full treatment or processing of the medical instruments occurs without the need to expose such instruments to the outer environment. The reprocessing device 1" comprises a housing 2", preferably made of plastic, with a door 21, which closes a maintenance chamber (not shown) arranged inside of the housing 2". Several connection ports for medical or dental instruments are provided in the chamber. Through the ports cleaning, disinfection, sterilization and care agents can be transported into the interior of the medical instruments based on a media supply as mentioned above. Additionally, through nozzles, which are arranged in the maintenance chamber, the cleaning, disinfection, sterilization and care agents can be spread onto the outside of the medical instruments.

According to this embodiment, a control unit 4" of the reprocessing device 1" comprises a wireless communication device 5", which is capable of creating a wireless local area network 11 allowing the remote accessories 6, 7, 8, 9, 10, in particular a dental unit 10, a printer 8, a remote display 6, a remote evaluation unit 7 and a second cleaning, disinfection and care device 9 to communicate with the control unit 4" of the cleaning, disinfecting, care and sterilization device 1". In this embodiment, the wireless communication device 5" is non-detachably connected to the control unit 4" of the reprocessing device 1".

The wireless network interfaces of the accessories 6, 7, 8, 9, 10 to provide access to the wireless local area network 11 are either non-detachably connected to the accessories 6, 7, 8, 10, in particular connected to the electric components of the accessories, such as to the controller of the dental unit 10, the printer 8, the smart phone 6 or the remote evaluation unit 7, or are detachably connected to the accessories, such as to the control unit of the second cleaning, disinfection and care device 9 using a USB stick 14.

Furthermore, the wireless network interfaces are preferably designed to communicate with control units 4" of multiple cleaning, disinfection, care and/or sterilization devices 1" simultaneously. For example in this embodiment, the reprocessing device 1" enabling full processing of the medical instruments and a second cleaning, disinfection and care device 9 can be operated and controlled by the same accessory 6, in particular by the smart phone 6 based on the wireless local area network 11 created by the reprocessing device 1" and the wireless network interface housed in the smart phone 6. So the reprocessing device 1", in particular the created wireless local area network 11, preferably allows the accessories 6, 7, 9, 10 to communicate with each other, in particular to transmit data among each other.

To provide internet access for the reprocessing device 1" and for the accessories 6, 7, 8, 9, 10, the control unit 4" of the reprocessing device 1" comprises an internet bridge 13. In this embodiment the internet bridge 13 is comprises a cellular modem, which is detachably connected to the control unit 4" of the reprocessing device 1" by a wired connection 22. Thus it is possible to transmit for example maintenance requirements or service instructions from the reprocessing device 1", in particular from the control unit 4", or from the accessories 6, 7, 8, 9, 10 preferably to a central server of a service center of the manufacturer of the devices.

Within the scope of the present invention it is self-evident that the inventive device for cleaning, disinfecting, care and/or sterilizing medical or dental instruments according to the invention is not limited to the embodiments described here, but instead includes all embodiments which apply or include fundamentally analogous function principles. In addition, all the features of all the embodiments described and depicted here may be combined with one another.

What is claimed is:

1. A cleaning, disinfecting, care or sterilization device for at least one medical or dental instrument comprising
   a housing,
   a treatment chamber for receiving the at least one medical or dental instrument,
   a media supply for feeding media into or discharging media out of the treatment chamber, and
   a control unit operable to control or regulate a cleaning, disinfecting, care or sterilization process, wherein
   the control unit comprises a wireless communication device to communicate with at least one remote accessory of the cleaning, disinfecting, care or sterilization device, wherein
   the wireless communication device is designed to create a wireless local area network allowing the at least one remote accessory to communicate with the control unit of the cleaning, disinfecting, care or sterilization device.

2. The cleaning, disinfecting, care or sterilization device according to claim 1, wherein the wireless communication device is non-detachably connected to the control unit of the cleaning, disinfecting, care or sterilization device.

3. The cleaning, disinfecting, care or sterilization device according to claim 1, wherein the wireless communication device is detachably connected to the control unit of the cleaning, disinfecting, care or sterilization device.

4. The cleaning, disinfecting, care or sterilization device according to claim 3, wherein the wireless communication device is encapsulated in a housing to protect it from mechanical or chemical damage.

5. The cleaning, disinfecting, care or sterilization device according to claim 1, wherein the wireless communication device comprises a wireless access point designed to allow the at least one remote accessory to connect to the control unit of the cleaning, disinfecting, care or sterilization device.

6. The cleaning, disinfecting, care or sterilization device according to claim 1, wherein the control unit comprises an internet bridge configured to provide internet access for the cleaning, disinfecting, care and/or or sterilization device and/or or for the at least one accessory.

7. The cleaning, disinfecting, care or sterilization device according to claim 6, wherein the internet bridge comprises a cellular modem which is non-detachably or detachably connected to the control unit of the cleaning, disinfecting, care or sterilization device.

8. The cleaning, disinfecting, care or sterilization device according to claim 1, wherein the control unit is designed to activate the wireless communication device.

9. The cleaning, disinfecting, care or sterilization device according to claim 1, wherein the control unit is designed to automatically communicate with the at least one connected remote accessory depending on a process parameter or process state of the cleaning, disinfecting, care or sterilization device.

10. The cleaning, disinfecting, care or sterilization device according to claim 1, wherein the wireless communication device is configured to create the wireless local area network according the Wi-Fi standard.

11. An apparatus for cleaning, disinfecting, caring or sterilizing at least one medical or dental instrument comprising
a cleaning, disinfecting, care or sterilization device capable of creating a wireless local area network according to claim 1, and
at least one accessory for the cleaning, disinfecting, care or sterilization device, wherein the at least one accessory comprises a wireless network interface to provide access to the wireless local area network in order to communicate with the control unit of the cleaning, disinfecting, care or sterilization device.

12. The apparatus to claim 11, wherein the wireless network interface is non-detachably connected to the at least one accessory.

13. The apparatus according to claim 11, wherein the wireless network interface is detachably connected to the at least one accessory.

14. The apparatus according to claim 11, wherein the at least one accessory, in particular the wireless network interface, is designed to communicate with control units of multiple cleaning, disinfecting, care or sterilization devices simultaneously.

15. The apparatus according to claim 11, wherein the at least one accessory comprises at least one of: a rack or tray for holding the medical instrument, a printer, a pouch sealing device, a water supply or distiller, an adapter for the instrument, a test kit to evaluate a reprocessing process, an evaluation unit, a second cleaning, disinfection and care device, a dental unit, a mobile phone, or a remote display.

* * * * *